United States Patent
Jenkins et al.

(10) Patent No.: US 9,840,450 B2
(45) Date of Patent: Dec. 12, 2017

(54) ENERGETIC HIGH PRESSURE POLYMORPH OF CROCONIC ACID AND HIGH ENERGY COMPOSITIONS FORMED THEREFROM

(71) Applicant: THE UNITED STATES OF AMERICA AS REPRESENTED BY THE SECRETARY OF THE ARMY, Washington, DC (US)

(72) Inventors: Timothy A Jenkins, Bel Air, MD (US); Jennifer A. M. Ciezak-Jenkins, Bel Air, MD (US); Jennifer L Gottfried, Abingdon, MD (US); Rose A Pesce-Rodriguez, Elkridge, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 119 days.

(21) Appl. No.: 14/847,023

(22) Filed: Sep. 8, 2015

(65) Prior Publication Data
US 2017/0066706 A1    Mar. 9, 2017

(51) Int. Cl.
| | |
|---|---|
| *D03D 23/00* | (2006.01) |
| *D03D 43/00* | (2006.01) |
| *C07C 49/707* | (2006.01) |
| *C06B 43/00* | (2006.01) |

(52) U.S. Cl.
CPC ............ *C07C 49/707* (2013.01); *C06B 43/00* (2013.01); *C07B 2200/13* (2013.01)

(58) Field of Classification Search
USPC .......................... 149/92, 108.8, 109.4, 109.6
See application file for complete search history.

(56) References Cited

U.S. PATENT DOCUMENTS

| | | | | |
|---|---|---|---|---|
| 8,127,661 | B2 * | 3/2012 | Klotz | B30B 11/004 92/177 |
| 2006/0224022 | A1 * | 10/2006 | Kimura | C07C 45/30 568/364 |

FOREIGN PATENT DOCUMENTS

EP    1707552    10/2006

OTHER PUBLICATIONS http://www.chemspider.com/Chemical-Structure.476003.html (2015).*

* cited by examiner

*Primary Examiner* — James McDonough
(74) *Attorney, Agent, or Firm* — Robert Thompson

(57) ABSTRACT

Provided is a high pressure polymorph of croconic acid. The high pressure polymorph of croconic acid has an unexpectedly high energy release and is suitable for use in detonable compositions. The high pressure polymorph of croconic acid is recoverable to ambient conditions and exhibits only a modest increase in density but a greatly improved energy release.

6 Claims, 2 Drawing Sheets

ENERGETIC HIGH PRESSURE POLYMORPH OF CROCONIC ACID AND HIGH ENERGY COMPOSITIONS FORMED THEREFROM

GOVERNMENT INTEREST

The invention described herein may be manufactured, used, and licensed by or for the United States Government.

FIELD OF USE

The invention relates to the field of explosives. More specifically, compositions are provided that utilize a high pressure polymorph of croconic acid as a relatively stable high energy material to promote explosive capabilities without a significant increase in weight.

BACKGROUND

Energy yields of high explosives ranging from trinitrotoluene (TNT) to cyclotetramethylenetetranitramine (HMX) are only about 1.0 to about 1.5 (kcal/gm). Secondary burning of these high explosives in air at elevated temperatures raises the volumetric energy release to a range of about 5.6 to about 6.1 (kcal/cc). In prior attempts to improve the explosive capabilities of these materials, the addition of metals such as aluminum, uranium, or tungsten resulted in no significant improvement in energy yield or blast effectiveness. For example, in U.S. Pat. No. 3,111,439, it is disclosed that attempts have been made to increase the power of high explosives by incorporating therein finely divided aluminum, which serves to increase the amount of heat energy liberated during detonation. Upon detonation, these prior aluminized explosives release energy in the form of heat of the order of 1.2 to 1.5 times the amount of energy released during the detonation of a similar quantity of TNT. The known explosives of this type, however, are incapable of producing the maximum release of energy since sufficient quantities of aluminum are lacking, and thus portions of the available oxygen are expended on lower energy reactions.

To improve the foregoing disadvantages, and to improve the release of heat energy upon detonation by about 3 to 6.2 times the heat energy released upon the detonation of an equal weight of trinitrotoluene (TNT), one or more oxygen carriers and a metal, such as lithium or beryllium, may be added to high explosive compounds. Heat is generated upon the formation of the oxides. All of the oxygen of the carrier must be utilized in the formation of the metallic oxides to realize the improved generation of heat. However, oxygen carriers are undesirable and add to the bulk and weight of the explosive composition. Furthermore, the weight of the oxidizers dilute the explosive component by reducing the amount of explosive that can be incorporated in the explosive mass, i.e., the oxidizers occupy space that would be better occupied by explosive materials or other energy releasing components. In addition, such applications are limited by side reactions with atmospheric reactants such as water, which forms $HBO_2$ (or HOBO) and other undesirable products that reduce heat output.

In addition to sufficient energy release, explosive compositions must also exhibit sufficient handling properties to provide safety in packaging and use and to prevent unwanted accidental detonation. Historical production of high energy materials with suitable handling properties and low risk of unwanted detonation has typically followed a few common pathways. The first is to combine a high energy material with an energetic binder such as trinitrotoluene or nitrocellulose. Such compositions reduce the amount of energetic material, but remain too unstable for modern use. A second path is to increase the amount of high energy material, but combine it with an inert binder such as an organic wax or polymer. The problem becomes finding the right balance of high energy material and inert binder to provide the necessary balance of explosive power and safety. The final approach is to synthesize new high energy compositions that may inherently possess the right balance of explosive power and insensitivity to unwanted detonation.

Further adding complexity to methods of crafting an explosive material with the proper power and safety is the fact that there are different types of packaging or uses that dictate physical characteristics of the material either during production or use. Castable explosives, as one type, are classified either as melt-cast or as plastic bonded. Melt-cast systems require the melting of the explosive, for example TNT (m.p. 81° C.), and casting into a munition. Plastic bonded systems involve a mixture of one or more explosives with a polymeric binder, casting into a munition or mold, and curing of the binder. Thus, any compositions for improving safety or handling properties of the energetic material must have the physical characteristics that allow them to function in either a melt-castable system or a plastic bonded system as desired.

The explosive formulations developed to date using the techniques described above have not yielded high energy output explosives that demonstrate a low enough susceptibility to unwanted or accidental detonation. Previous efforts have failed in this respect in that they did not discover the proper combination filler or binder (i.e. in either chemical type or concentration level) to yield these properties.

As such, there is a need for new explosive compositions with enhanced detonation yet safe handling properties.

SUMMARY

The following summary is provided to facilitate an understanding of some of the innovative features unique to the present invention and is not intended to be a full description. A full appreciation of the various aspects of the invention can be gained by taking the entire specification, claims, drawings, and abstract as a whole.

Provided is a high pressure polymorph of croconic acid that demonstrates unexpectedly superior explosive capability and excellent safety. It was found that by compressing croconic acid to a suitable pressure for a suitable compression time that an ambient condition recoverable high pressure polymorph of the croconic acid was produced. The high pressure polymorph of croconic acid optionally has a density of 1.95 $g/cm^3$ to 2.5 $g/cm^3$, optionally 2.1 $g/cm^3$. The high pressure polymorph of croconic acid has an unexpectedly superior explosive capability, optionally with a laser shock velocity in excess of 800 meters per second.

The high pressure polymorph of croconic acid is optionally used in a detonable composition that includes a high pressure polymorph of croconic acid with a laser shock velocity in excess of 800 m/s. The detonable composition optionally excludes or includes a binder, a secondary high energy material, or other safety or other additive. However, a detonable composition may include a secondary high energy material. A secondary high energy material is optionally: 1,3,5-trinitro-1,3,5-triazacyclohexane (1,3,5-trinitroperhydro-1,3,5-triazine; RDX); 1,3,5,7-tetranitro-1,3,5,7-tetrazocane (1,3,5,7-tetranitro-1,3,5,7-tetrazocane; HMX); 2,2-bis(hydroxymethyl)1,3-propanediol (pentaerythritol tetranitrate; PETN); 2,4,6-trinitrotoluene (2-methyl-1,3,5-trinitrobenzene; TNT), 1,2,3-trinitroxypropane (trinitroglycerin; TNG); 2,3-dimethyl-2,3,-dinitrobutane (2,3-dimethyl-2,3-dinitrobutane; DMDNB); triacetone triperoxide (TATP); hexamethylene triperoxide diamine (HMTD); other peroxide or nitrate based explosive materials; gunpowder(s); pentaerythritol (2,2-Bis(hydroxymethyl)1,3-propanediol; PE); military or commercial grades of C4; Semtex A1; Semtex H; 2,4-dinitroanisole (DNAN), 1,3-Dinitrobenzene (1,3-DNB); 1,3,5-Trinitrobenzene (1,3,5-TNB); hexanitrostilbene (HNS); croconic acid; pentolite; 2,4,6-triamino-1,3,5-trinitrobenzene (TATB); comp B; nitrotriazalone (NTO); hexanitrohexaazaisowurtzitane (CL-20); 1,1-diamino-2,2-dinitroethene (DADNE; FOX-7); or combinations thereof.

Also provided are processes of forming a high pressure polymorph of croconic acid including subjecting croconic acid to a pressure of 5 gigaPascals or greater for a compression time. A compression time is optionally 12 to 20 hours, or any value or range therebetween. The step of subjecting is optionally at a temperature between 5° C. and 45° C., optionally 25° C. A compression pressure is optionally 5 GPa or greater, optionally between 5 and 9 GPa, optionally 9 GPa, optionally greater than 9 GPa.

The resulting high pressure polymorph of croconic acid addresses the need for new explosive compositions with enhanced detonation yet safe handling properties.

DETAILED DESCRIPTION

Figure 1:
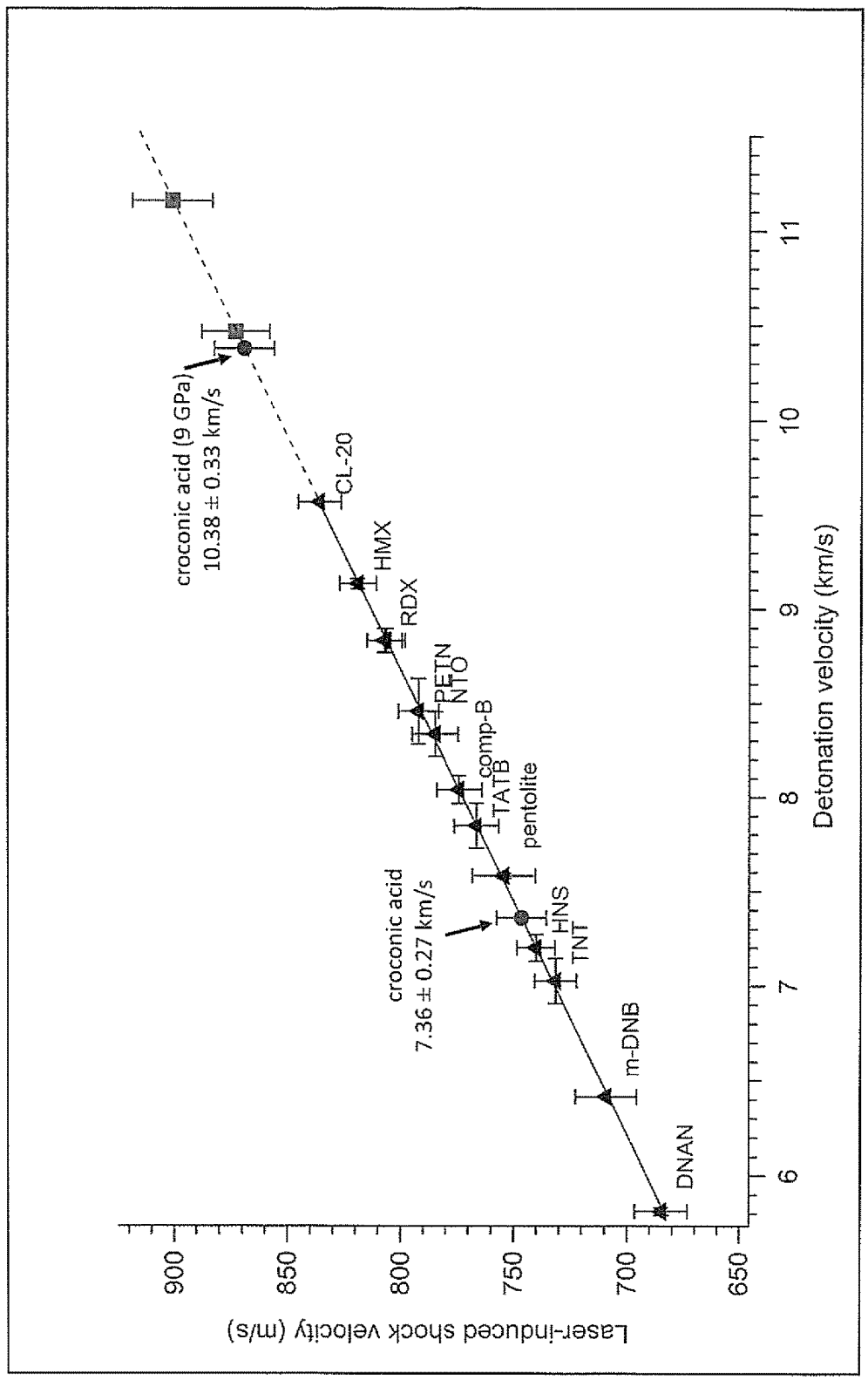
FIG. 1 illustrates laser shock velocity of various energetic materials including croconic acid in the standard crystal form and the high pressure polymorph of croconic acid with much greater energy output.

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

The terminology used herein is for the purpose of describing particular aspects only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

As defined herein, the term "high energy" is defined as a material possessing a laser shock velocity of 650 m/s or greater under the conditions of Gottfried, J L, *Phys. Chem. Chem. Phys.*, 2014, 16, 21452.

As defined herein, the term "binder" is a synthetic polymer which is used in small quantities (typically 5-10% by weight) to bind together an explosive powder.

Increasing energy density in explosive systems is highly desirable to provide improved explosive capability and to reduce weight and or size of the required explosive material necessary. While several types of high energy explosive materials are available, many of these such as CL-20, require the inclusion of binders to increase the stability of the explosive materials for ease and safety of handling to reduce the likelihood of unwanted shock or friction detonation.

Provided is a high pressure polymorph of croconic acid (4,5-dihydroxy-4-cyclopentene-1,2,3-trione) that has utility as a high energy explosive composition for use in military or mining applications, or any other application requiring explosive materials. The high pressure polymorph of croconic acid is formed by compression of croconic acid to a pressure of 5 GPa or greater for a compression time. Following compression of the croconic acid, the crystal space group remains the same but has altered lattice parameters relative to non-compressed croconic acid (Pca2). The high pressure polymorph of croconic acid is recoverable to ambient conditions or temperature and pressure, as well as exhibits excellent explosive capability and handling stability. In some aspects, handling stability is measured by drop height sensitivity, electrostatic discharge, and friction sensitivity, all determined per standard measuring techniques for explosives. A safe material optionally has an impact sensitivity of greater than 60 inches, optionally an electrostatic discharge in excess of 1 J, optionally in excess of 6.25 J, and/or optionally a friction sensitivity of greater than 120 N, optionally greater than 353 N, or combinations thereof. The high pressure polymorph of croconic acid has an impact sensitivity in excess of 60 inches, an electrostatic discharge in excess of 6.25 J, and a friction sensitivity in excess of 353 N.

Croconic acid is optionally commercially available croconic acid such as that obtained from TCI-America (Portland, Oreg.). The croconic acid is compressed to a structural conversion pressure for a compression time. Pressurization is optionally achieved using a Paris-Edinburgh design pressure cell (PEC) employing toroidal tungsten carbide or sintered diamond anvils. PECs, originally developed in 1992 are capable of exhibiting pressures on relatively large volumes of material to a level of up to 10-20 GPa. A structural conversion pressure is optionally 5 GPa or greater, optionally 9 GPa (1,305,340 psi) or greater. As such the term "high pressure" refers to the material having been subjected to a pressure of 5 GPa or greater. In some aspects, the entire sample is subjected to a pressure of 5 GPa or greater meaning that the entire volume of material is subjected to such a compression pressure. Without being limited to one particular theory, when compressing materials at microgram quantities or greater, it is believed that a pressure gradient is created across the material resulting in greater compression of the material in the outer regions relative to the inner regions of a sample. Thus, by subjecting the croconic acid to a pressure of 5 GPa, optionally 6.5 GPa, optionally 7 GPa, optionally 7.5 GPa, optionally 8 GPa, optionally 8.5 GPa, optionally 9 GPa, the entire sample is converted to the high pressure polymorph resulting in 100% yield of the high pressure polymorph material from the sample.

Croconic acid is compressed for a compression time. A compression time is any time suitable to change the crystal form of the material when compressed at a structural conversion pressure. A compression time is optionally 12 to 20 hours, or any value or range therebetween. A compression time is optionally 12, 13, 14, 15, 16, 17, 18, 19, or 20 hours.

During the compression of croconic acid, the temperature is optionally held constant to ambient temperature or 25° C. (+/−20° C.).

The high pressure polymorph of croconic acid has a density ranging from 1.95 g/cm$^3$ to 2.5 g/cm$^3$, or any value or range therebetween. In some aspects, a high pressure polymorph of croconic acid has a density of 2.0 g/cm$^3$, optionally 2.1 g/cm$^3$, optionally 2.2 g/cm$^3$, optionally 2.3 g/cm$^3$, optionally 2.4 g/cm$^3$, optionally 2.5 g/cm$^3$.

A high pressure polymorph of croconic acid has a laser shock velocity that is greater than simple croconic acid (not subjected to sufficient compression). Laser shock velocity of a high pressure polymorph of croconic acid optionally has a laser shock velocity in excess of 760 m/s when measured by the process of Gottfried, J L, *Phys. Chem. Chem. Phys.*, 2014, 16, 21452. A high pressure polymorph of croconic acid optionally has a laser shock velocity of 770 m/s or greater, optionally 780 m/s or greater, optionally 790 m/s or greater, optionally 800 m/s or greater, optionally 810 m/s or greater, optionally 820 m/s or greater, optionally 830 m/s or greater, optionally 840 m/s or greater, optionally 850 m/s or greater, optionally 860 m/s or greater, optionally 870 m/s or greater, optionally 880 m/s or greater. In some aspects, a high pressure polymorph of croconic acid has a laser shock velocity of between 850 m/s to 880 m/s.

The many advantages of this material over existing explosives relate to the performance characteristics and the ease of synthesis. There are several energetic materials such as HMX, RDX, and CL-20 that are synthesized by chemical reactions in a traditional fashion suffering material loss at each step. The obtained high pressure polymorph of croconic acid, in contrast, is produced from a single step synthesis that does not suffer from losses during chemical synthesis. Thus, the efficiency of formation of the high pressure polymorph of croconic acid greatly exceeds that of comparative materials.

The high pressure polymorph of croconic acid created by compression at 9 GPa has a density of 2.1 g/cm$^3$, relative to 2.044 g/cm$^3$ of hexanitrohexaazaisowurtzitane (2,4,6,8,10,12-hexanitro-2,4,6,8,10,12-hexaazaisowurtzitane; CL-20) and 1.816 g/cm$^3$ of 1,3,5-trinitro-1,3,5-triazacyclohexane (1,3,5-trinitroperhydro-1,3,5-triazine; RDX). This means that the high pressure polymorph of croconic acid exhibits only a 3% increase in mass for the same volume compared to CL-20. The relatively low increase in mass will allow for easy packaging in systems that require either low amounts of high energy explosive materials or will allow large amounts to be packaged thereby increasing overall explosive yield for charge size.

The high pressure polymorph of croconic acid was assessed for explosive capability by laser shock velocity. Laser shock velocity was assessed essentially as described by Gottfried, J L, *Phys. Chem. Chem. Phys.*, 2014, 16, 21452. Briefly, a 10 mg to 20 mg sample of the test material (e.g. high pressure polymorph of croconic acid, or other material for testing as illustrated in FIG. 1), is placed onto two-sided tape affixed to a glass microscope slide (25 mm×75 mm) and spread across the surface. Excess was removed by tapping the slide. The sample was subjected to laser energy produced by a Nd:YAG laser focused on the sample with a 10 cm lens where the laser included the following parameters: pulse wavelength—1064 nm; pulse duration—6 ns; maximum pulse energy—900 mJ; spot area—$5 \times 10^{-3}$ cm$^2$; fluence—180 J/cm$^2$; and irradiance—$3 \times 10^{10}$ W/cm$^2$. The plane of the target was placed 1.5 mm above the focal point of the lens. The schlieren imaging technique (G. S. Settles, *Schlieren and Shadowgraph Techniques*, Springer-Verlag, New York, 2001) was used to visualize the laser-induced shock wave in air. A high-speed color camera (Photron SA5) was used to record the light and dark striations in the images representing differences in the refractive index of air in the test region. Shock position in each image frame was measured to obtain resulting shock wave velocity. Results are depicted in FIG. 1. These results indicate the potential for significant increase in energy over current energetics, and demonstrate the enhancement achieved from the high pressure compression of croconic acid to a new recoverable pressure phase (high pressure polymorph). By relating laser shock velocity to detonation velocity, the detonation velocity of a larger scale test can be predicted. The predicted detonation velocity is 10.38 km/s for the high pressure polymorph of croconic acid vs. a measured detonation velocity of 9.57 km/s for CL-20 and 8.833 km/s for RDX.

Figure 2:
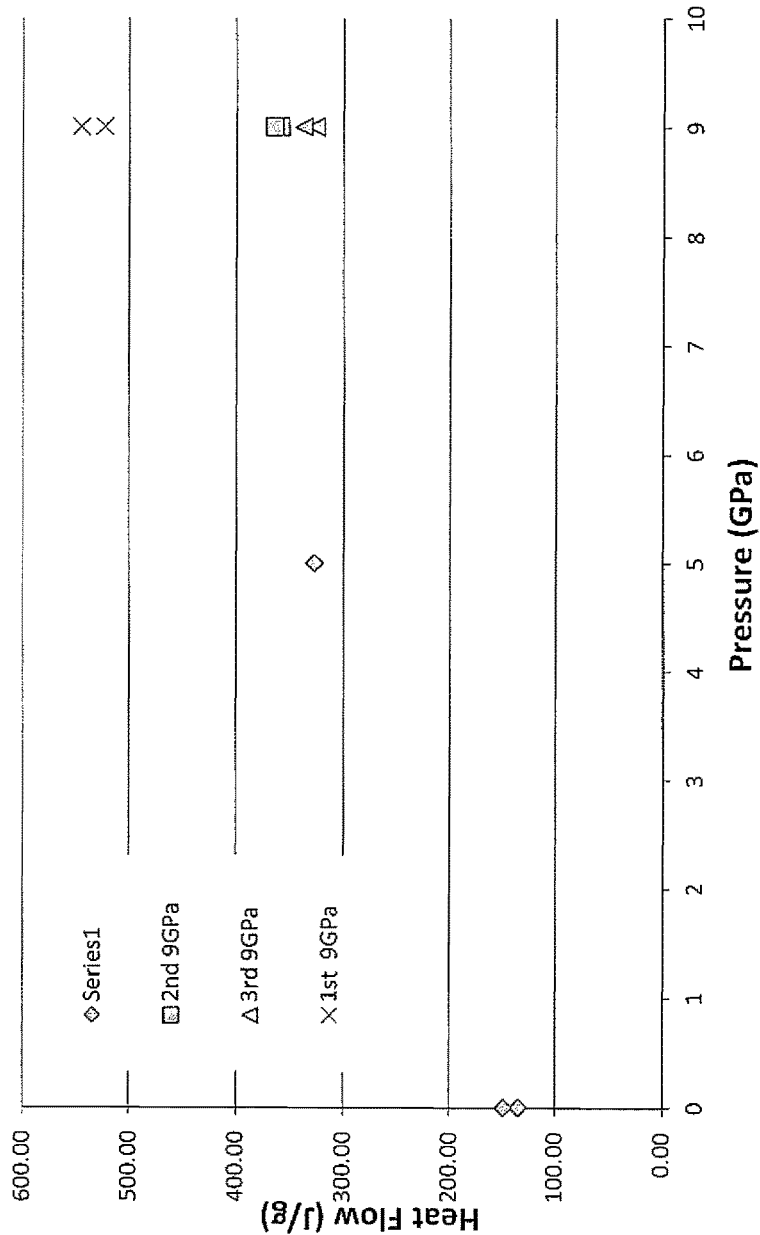
FIG. 2 illustrates differential scanning calorimetry obtained on the high pressure polymorph of croconic acid obtained either before compression, or after compression at 5 GPa or 9 GPa.

In addition, samples of various materials including the high pressure polymorph of croconic acid and RDX were analyzed by differential scanning calorimetry (DSC). DSC measurements were performed on a TA instruments 010 or 020 calorimeter calibrated to the melting point of indium. The results for the high pressure polymorph of croconic acid are illustrated in FIG. 2. The results demonstrate a heat flow in excess of 300 J/g following compression at 5 GPa and 9 GPa. This compares to 2000 J/g for RDX (not shown).

The high pressure polymorph of croconic acid is optionally included in a detonable composition. A detonable composition optionally is or includes the high pressure polymorph of croconic acid.

A detonable charge optionally includes a high pressure polymorph of crononic acid alone or in combination with one or more secondary high energy materials, a binder, a plasticizer, or any combination thereof. A secondary high energy material is optionally any material with a laser shock velocity as measured herein of 650 m/s or greater, optionally 700 m/s or greater. In some aspects, a secondary high energy material is 1,3,5-trinitro-1,3,5-triazacyclohexane (1,3,5-trinitroperhydro-1,3,5-triazine; RDX); 1,3,5,7-tetranitro-1,3,5,7-tetrazocane (1,3,5,7-tetranitro-1,3,5,7-tetrazocane; HMX); 2,2-bis(hydroxymethyl)1,3-propanediol (pentaerythritol tetranitrate; PETN); 2,4,6-trinitrotoluene (2-methyl-1,3,5-trinitrobenzene; TNT), 1,2,3-trinitroxypropane (trinitroglycerin; TNG); 2,3-dimethyl-2,3,-dinitrobutane (2,3-dimethyl-2,3-dinitrobutane; DMDNB); triacetone triperoxide (TATP); hexamethylene triperoxide diamine (HMTD); other peroxide or nitrate based explosive materials; gunpowder(s); pentaerythritol (2,2-Bis(hydroxymethyl) 1,3-propanediol; PE); military or commercial grades of C4; Semtex A1; Semtex H; 2,4-dinitroanisole (DNAN), 1,3-Dinitrobenzene (1,3-DNB); 1,3,5-Trinitrobenzene (1,3,5-TNB); hexanitrostilbene (HNS); croconic acid; pentolite; 2,4,6-triamino-1,3,5-trinitrobenzene (TATB); comp B; nitrotriazalone (NTO); hexanitrohexaazaisowurtzitane (CL-20); 1,1-diamino-2,2-dinitroethene (DADNE; FOX-7); or combinations thereof. A secondary high energy material is optionally present at 25% to 75% by weight, or any value or range therebetween.

A detonable charge optionally includes one or more binders or one or more plasticizers. Some aspects of a detonable charge optionally exclude an energetic binder, an inert binder or both. Some known "energetic" binders used in a detonable charge include nitrocellulose, nitrostarch, polyvinylnitrate, and nitropolyurethanes. Some known inert binders used in used in a detonable charge include cellulose acetate (CA), cellulose acetate butyrate (CAB), hydroxy-terminated polybutadiene (HTPB), and polyurethanes. Some conventional energetic plasticizers used in detonable charges are: BDNPF (Bis-2,2-Dinitropropyl Fumarate); NG (Nitroglycerin); Methyl/Ethyl Nena; Butyl Nena; MTN/DEGDN (Metriol trinitrate/Diethylene Glycol Dinitrate); and DEGDN (Diethylene Glycol Dinitrate). Some conventional inert plasticizers used in detonable charges include: TA (Triacetin); DEP (Diethyl Phathalate); and DBP (Dibutyl Phathalate). A binder, if present, is optionally included at an amount of 1% to 20% by weight. A plasticizer, if present, is optionally included at an amount of 1% to 20% by weight.

A detonable charge may be produced through standard production methods such as melt-casting or pressing the charges. The technique selected for charge production is governed by several formulation parameters such as melt temperatures and small scale sensitivity testing results.

The detonable composition can be compounded, mixed, and formulated in any well-known manner for making explosive compositions. Some aspects of making a detonatable composition include mixing the high pressure polymorph of croconic acid alone or along with one or more of a secondary high energy material, optionally one or more fuel additives, optionally one or more oxidixers, and optionally one or more plasticizers in the desired stoichiometric quantities. The particles or powders may be mixed in a blender and are formed into pellets by means of pressure in a conventional pelletizing operation. The pelletized aggregate or mixture is optionally encapsulated by conventional techniques.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

We claim:

1. A detonable composition comprising:
   a high pressure polymorph of croconic acid with a laser shock velocity in excess of 800 meters per second;
   excluding a binder; and
   further comprising a secondary high energy material.

2. The detonable composition of claim 1 wherein said secondary high energy material is selected from the group consisting of 1,3,5-trinitro-1,3,5-triazacyclohexane (1,3,5-trinitroperhydro-1,3,5-triazine; RDX); 1,3,5,7-tetranitro-1,3,5,7-tetrazocane (1,3,5,7-tetranitro-1,3,5,7-tetrazocane; HMX); 2,2-bis(hydroxymethyl)1,3-propanediol (pentaerythritol tetranitrate; PETN); 2,4,6-trinitrotoluene (2-methyl-1,3,5-trinitrobenzene; TNT), 1,2,3-trinitroxypropane (trinitroglycerin; TNG); 2,3-dimethyl-2,3,-dinitrobutane (2,3-dimethyl-2,3-dinitrobutane; DMDNB); triacetone triperoxide (TATP); hexamethylene triperoxide diamine (HMTD); other peroxide or nitrate based explosive materials; gunpowder(s); pentaerythritol (2,2-Bis(hydroxymethyl) 1,3-propanediol; PE); military or commercial grades of C4; Semtex A1; Semtex H; 2,4-dinitroanisole (DNAN), 1,3-Dinitrobenzene (1,3-DNB); 1,3,5-Trinitrobenzene (1,3,5-TNB); hexanitrostilbene (HNS); croconic acid; pentolite; 2,4,6-triamino-1,3,5-trinitrobenzene (TATB); comp B; nitrotriazalone (NTO); hexanitrohexaazaisowurtzitane (CL-20); 1,1-diamino-2,2-dinitroethene (DADNE; FOX-7); and combinations thereof.

3. A process of forming a high pressure polymorph of croconic acid comprising: subjection croconic acid to a pressure of 5 giga Pascals or greater for a compression time.

4. The process of claim 3 wherein said compression time is 12 to 20 hours.

5. The process of claim 3 where said step of subject is at a temperature of 5 degrees Celsius to 45 degrees Celsius.

6. The process of claim 3 wherein said pressure is 9 gigaPascals.

* * * * *